United States Patent [19]

DeGroot et al.

[11] Patent Number: 5,438,126

[45] Date of Patent: Aug. 1, 1995

[54] HUMAN THYROID HORMONE RECEPTOR DNA

[75] Inventors: Leslie J. DeGroot; Akira Nakai, both of Chicago, Ill.

[73] Assignee: Arch Development Corporation, Chicago, Ill.

[21] Appl. No.: 830,766

[22] Filed: Feb. 3, 1992

Related U.S. Application Data

[63] Continuation of Ser. No. 405,342, Sep. 11, 1989, abandoned.

[51] Int. Cl.$^6$ .................. C12Q 1/68; C07H 21/14; C07K 14/435
[52] U.S. Cl. .................. 536/23.5; 435/69.1; 435/240.2; 435/9.4; 435/320.1; 935/11; 935/23
[58] Field of Search .................. 536/27–29, 536/23.5; 435/6, 172.6, 240.2; 935/11, 23

[56] References Cited

U.S. PATENT DOCUMENTS

| | | | |
|---|---|---|---|
| 4,683,195 | 7/1987 | Mullis | 435/6 |
| 4,683,202 | 7/1987 | Mullis | 435/91 |
| 4,719,177 | 1/1988 | Baltimore et al. | 435/91 |

OTHER PUBLICATIONS

Benbrook, D., et al., Science, 238:788–791 1987.
Catanzaro, D. F., et al., Molecular Endocrinology, 1:90–96 (1987).
Chirgwin, J. M. et al., Biochemistry, 18:5294–5299 (1987).
Gustafson, T. A., et al., Proc. Nat'l. Acad. Sci. (USA), 84:3122–3126 (1979).
Hollenberg, S. M., et al., Nature, 318:635–641 (1985).
Koenig, M., et al., Cell, 50:509–517 (1987).
Larsen, P. R., et al., J. Biol. Chem., 261:14373–14376 (1986).
Lewin, B., Cell, 22:324–326 (1980).
Melton, D. A., et al., Nucleic Acids Research, 12:7035–7056 (1984).
Nakai, A., et al., Proc. Nat'l. Acad. Sci. (USA), 85:2781–2785 (1988).
Saiki, R. K., et al., Science, 230:1350–1354 (1985).
Sanger, F., et al., Proc. Nat'l Acad. Sci. (USA), 74:5463–5467 (1977).
Sap, J., et al., Nature, 324:635–640 (1986).
Thompson, C. C., et al., Science, 237:1610–1614 (1987).
Weinberger, C., et al., Nature, 324:641–646 (1986).
Ye, Z-S., et al., J. Biol. Chem., 262:6313–6317 (1986).
Nakai et al. Mol. Endocrinology, vol. 2, pp. 1087–1092, 1988.
Alberts et al. The Molecular Biology of the Cell, Garland Publishing: New York, 1983, pp. 189–190.

*Primary Examiner*—Douglas W. Robinson
*Assistant Examiner*—Gary L. Kunz
*Attorney, Agent, or Firm*—Arnold, White & Durkee

[57] ABSTRACT

The DNA encoding human thyroid hormone receptor protein alpha-1 (hTR −1). This polynucleotide can be used as a probe to detect the presence of a third form of human thyroid hormone receptor protein.

5 Claims, 3 Drawing Sheets

FIG. 1A

```
 1    TGCCGGGGGGCCAGTGTGCCCACCCCAGTCTCTTGGCTGTGCTGAGGGCATCCTGGATGGAATTGAAGTGA 1                                    10                                   20
 73   Met Glu Gln Lys Pro Ser Lys Val Glu Cys Gly Ser Asp Pro Glu Asn Ser Ala Arg Ser Pro
      ATG GAA CAG AAG CCA AGC AAG GTG GAG TGT GGG TCA GAC CCA GAG AAC AGT GCC AGG TCA CCA 30                                    40
 139  Asp Gly Lys Arg Lys Arg Lys Asn Gly Gln Cys Ser Leu Lys Thr Ser Met Ser Gly Tyr Ile Pro
      GAT GGA AAG CGA AAA AGA AAG AAC GGC CAA TGT TCC CTG AAA ACC AGC ATG TCA GGG TAT ATC CCT 50                                    60
 205  Ser Tyr Leu Asp Lys Asp Lys Glu Gln Gln Cys Val Val Cys Gly Asp Lys Ala Thr Gly Tyr His Tyr Arg
      AGT TAC CTG GAC AAA GAC AAA GAG CAG CAG TGT GTC GTG TGT GGG GAC AAG GCA ACT GGT TAT CAC TAC CGC 70                                    80
 271  Cys Ile Thr Cys Glu Gly Cys Lys Gly Phe Phe Arg Arg Thr Ile Gln Lys Asn Leu His Pro Thr
      TGT ATC ACT TGT GAG GGC TGC AAG GGC TTT TTC CGC CGC ACA ATC CAG AAG AAC CTC CAT CCC ACC 90                                   100                                   110
 337  Tyr Ser Cys Lys Tyr Asp Ser Cys Cys Val Ile Asp Lys Ile Thr Arg Asn Gln Cys Gln Leu Cys
      TAT TCC TGC AAA TAT GAC AGC TGT TGT GTC ATT GAC AAG ATC ACC CGC AAT CAG TGC CAG CTG TGC 120                                   130
 403  Arg Phe Lys Lys Cys Ile Ala Val Gly Met Ala Met Asp Leu Val Leu Asp Asp Ser Lys Arg Val
      CGC TTC AAG AAG TGC ATC GCC GTG GGC ATG GCC ATG GAC CTT GTT CTA GAT GAC TCG AAG CGG GTG 140                                   150
 469  Ala Lys Arg Lys Leu Ile Glu Gln Asn Arg Glu Arg Arg Arg Lys Glu Glu Met Ile Arg Ser Leu
      GCC AAG CGT AAG CTG ATT GAG CAG AAC CGG GAG CGG CGG AGG AAG GAG GAG ATG ATC CGA TCA CTG 160                                   170
 535  Gln Gln Arg Pro Glu Pro Thr Pro Glu Glu Trp Asp Leu Ile His Ile Ala Thr Glu Ala His Arg
      CAG CAG CGA CCA GAG CCC ACT CCT GAA GAG TGG GAT CTG ATC CAC ATT GCC ACA GAG GCC CAT CGC
```

FIG. 1B

```
                                          180
601   Ser Thr Asn Ala Gln Gly Ser His Trp Lys Gln Arg Arg Lys Phe Leu Pro Asp Asp Ile Gly Gln
      AGC ACC AAT GCC CAG GGC AGC CAT TGG AAA CAG AGG CGG AAA TTC CTG CCC GAT GAC ATT GGC CAG
                                                            190                            220
667   Ser Pro Ile Val Ser Met Pro Asp Gly Asp Lys Val Asp Leu Glu Ala Phe Ser Glu Phe Thr Lys
      TCA CCC ATT GTC TCC ATG CCG GAC GGA GAC AAG GTG GAC CTG GAA GCC TTC AGC GAG TTT ACC AAG
          200                                 210                                      240
733   Ile Ile Thr Pro Ala Ile Thr Arg Val Val Asp Phe Ala Lys Lys Leu Pro Met Phe Ser Glu Leu
      ATC ATC ACC CCG GCC ATC ACC CGT GTG GTG GAC TTT GCC AAA AAA CTG CCC ATG TTC TCC GAG CTG
                                      230                                      240
799   Pro Cys Gly Asp Gln Ile Ile Leu Leu Lys Gly Cys Cys Met Glu Ile Met Ser Leu Arg Ala Ala
      CCT TGC GGA GAC CAG ATC ATC CTC CTC AAG GGG TGC TGC ATG GAG ATC ATG TCC CTG CGG GCG GCT
                                              250                              260
865   Val Arg Tyr Asp Pro Glu Ser Asp Thr Leu Thr Val Ser Asp Ala Ile Met Gly Glu Met Ala Val
      GTC CGC TAC GAC CCT GAG AGC GAC ACC CTG ACG GTA TCC GAC GCC ATC ATG GGG GAG ATG GCT GTC
                                  270                                      280
931   Lys Asn Gly Gly Leu Gly Val Val Ser Asp Ala Ile Phe Glu Leu Gly Lys Ser Leu Ser Ala Leu
      AAG AAT GGC GGC CTG GGC GTA TCC GAC GCC ATC TTT GAA CTG GGC AAG TCA CTC TCT GCC CTG
                                          290                            300
997   Phe Asn Leu Asp Asp Thr Glu Val Ala Leu Leu Gln Ala Val Leu Leu Met Ser Thr Asp Arg Ser
      TTT AAC CTG GAT GAC ACG GAA GTG GCT CTG CTG CAG GCT GTG CTA CTA ATG TCA ACA GAC CGC TCG
                              310                              320                      330
1063  Gly Leu Leu Cys Val Asp Lys Ile Glu Lys Ser Gln Glu Ala Tyr Leu Leu Ala Phe Glu His Tyr
      GGC CTG CTG TGT GTG GAC AAG ATC GAG AAG AGT CAG GAG GCG TAC CTG CTG GCG TTC GAG CAC TAC
                                      340                                      350
```

```
                     360                              370
1129  Val Asn His Arg Lys His Asn Ile Pro His Phe Trp Pro Lys Leu Leu Met Lys Val Thr Asp Leu
      GTC AAC CAC CGC AAA CAC AAC ATT CCG CAC TTC TGG CCC AAG CTG ATG AAG GTG ACT GAC CTC
                                           380                              390
1195  Arg Met Ile Gly Ala Cys His Ala Ser Arg Phe Leu His Met Lys Val Glu Cys Pro Thr Glu Leu
      CGC ATG ATC GGG GCC TGC CAC GCC AGC CGC TTC CTC CAC ATG AAA GTC GAG TGC CCC ACC GAA CTC
                   400                              410
1265  Phe Pro Pro Leu Phe Leu Glu Val Phe Glu Asp Gln Glu Val
      TTC CCC CCA CTC TTC CTC GAG GTC TTT GAG GAT CAG GAA GTC TAA AGCCTCAGGGCGGCCAGAGGGTGTGCGG

1333  AGCTGGTGGGAGAGCCTGGAGAGAAGGGGCAGAGCTGGGGGCAGACCCCCACACACACCCCCTTCTCTCCTTCCTCTCGTCC

1420  TTGGATAGATTCAGTCTCCCACACACACACCCCGCACTGCCCAGGTCCCTCCAGACCTCCAGCCCTGGGACAGGGCAAACAACTGA

1507  ACTTGCTATGGAAAGGACAGTGTGGGAGGCTGGGAGCTGTGTCCAGTTCCCAGGACCCCATCCTCTCAGAAGGTAGGGAAG

1594  GGCGGGAGGATTGAGAAGGACAAGCCACCTTGACCGTAGGGGAAGGAGGAATGTGGGCTGGGGAAGATGCCCTCAACTCACCCCC

1681  TCACACACATGAGAGAGAGAGAGCCCCCACCCAGTTCCTTGGCCTAGGTCTCCCCCTGAGGGCTGAGGGCCTCTCTCTACTTCCCCAGATGCCT

1768  GGGTGCAAAGAACGGCTTGGCTCCTCCTCCTCTGGAGGTTAAAATTTATAGTCATTCTAACTGCACTTGGAAACCAAGCAAGGGG

1855  AGAAGACAAATGAAGAAAAACTAAAAAAAAAAAAAAAAAA
```

FIG. 1C

HUMAN THYROID HORMONE RECEPTOR DNA

The United States Government may have certain rights in the present invention pursuant to grant number USPHS DK 13377.

This application is a continuation, of application Ser. No. 07/405,342, filed Sep. 11, 1989, now abandoned.

BACKGROUND OF THE INVENTION

The present invention relates generally to DNA sequences encoding human thyroid hormone receptor proteins and more particularly to DNA sequences encoding human thyroid hormone receptor protein designated hTRα1, to the polypeptide products of recombinant expression of these DNA sequences, to peptides whose sequences are based on amino acid sequences deduced from these DNA sequences, to antibodies specific for such proteins and peptides, and to procedures for detection and quantification of such proteins and nucleic acids related thereto.

The physiological and developmental effects of thyroid hormone are mediated by a family of thyroid hormone receptors. The ligand-receptor complexes function as trans-acting transcriptional factors and exert their effects by binding to specific sequences in thyroid hormone responsive genes. (Larsen, P. R., et al., *J. Biol. Chem.*, 261:14373–14376 (1986); Catanzaro, D. F., et al., *Mol. Endocrinol.*, 1:90–96 (1987); Ye, Y. S., *J. Biol. Chem.*, 262:6313–6317 (1986); Gustafson, T. A., et al., *Proc. Nat'l. Acad. Sci. (USA)*, 84:3122–3126 (1987)). In humans, two different types of thyroid hormone receptors (TR) have been described. One, designated human TRβ(hTRβ), is encoded by a gene on chromosome 3 and is expressed in placenta and several cell lines. (Weinberger, C., et al., *Nature*, 324:641–648 (1986)). The second, designated human TRα2 (hTRα2), is encoded by a gene on chromosome 17 and is expressed in several tissues including kidney, testis, liver, and brain, as well as placenta (Benbrook, D., et al., *Science*, 238-788–791 (1987); Nakai, A., et al., *Proc. Nat'l. Acad. Sci. USA*, 85:2781–2785 (1988). cDNAs encoding other forms of thyroid hormone receptors have been isolated from a rat brain library (rTRα1) (Thompson, C. C., et al., *Science*, 237:1610–1614 (1987) and a chicken embryo library (cTRα). Sap, J., et al., *Nature*, 324:635–640 (1986).

Because of the possibility that additional forms of the thyroid hormone receptor might be expressed in human tissues, efforts have been directed towards isolating other putative receptors. The invention described herein relates, in part, to the results of these efforts.

Skeletal muscle is a thyroid hormone responsive tissue. Accordingly, a skeletal muscle cDNA library was screened for sequences that would cross-hybridize with the hTRα2 cDNA probe of the co-inventors herein. Nakai, A., et al., *PNAS USA*, 85:2781 (1988). A cDNA clone was isolated from this library and found to encode a unique form of the human thyroid hormone receptor that is closely related to the sequences of both hTRα2 and rTRα1. This third type of human thyroid hormone receptor, designated hTRα1, is expressed in many different tissues. Moreover, when expressed in vitro, a protein is produced which binds thyroid hormone with high affinity. A comparison of the sequences of hTRα1 and hTRα2 type thyroid hormone receptors suggests that they are likely encoded by the same gene and that alternative RNA splicing results in the synthesis of either hTRα1 or hTRα2.

BRIEF SUMMARY OF THE INVENTION

The present invention relates generally to hTRα1, to DNA sequences encoding hTRα1, to the polypeptide products of recombinant expression of these DNA sequences, to peptides whose sequences are based upon the amino acid sequences deduced from these DNA sequences, to antibodies specific for such proteins and peptides, to procedures for the detection and quantitation of such proteins and nucleic acids related thereto, as well as to procedures relating to the development of therapeutic agents.

In presently preferred forms, novel DNA sequences comprise cDNA sequences encoding hTRα1 protein. Specifically, this sequence is contained in the plasmid designated pMe21. Alternate DNA forms, such as genomic DNA, and DNA prepared by partial or total chemical synthesis from nucleotides, as well as DNA with deletions or mutations, is also within the contemplation of the invention. Also provided are novel messenger RNA (mRNA) sequences, specifically hTRα1 mRNA species.

Association of DNA sequences provided by the invention with homologous or heterologous species expression control DNA sequences, such as promoters, operators, regulators, and the like, allows for in vitro transcription to form mRNA which, in turn, is susceptible to translation to provide hTRα1 proteins, and related poly- and oligo-peptides in large quantities.

In a presently preferred in vitro DNA expression system of the invention, hTRα1 encoding DNA is inserted into the EcoR1 site of plasmid pGEM4Z and the resulting plasmid, designated pMe21 is linearized and used as a template for the SP6 polymerase catalyzed synthesis of RNA. Capped RNA is then translated in a rabbit reticulocyte system to provide two major forms of hTRα1 protein, including 55 and 50 kD species, capable of demonstrating functional characteristics of native hTRα1 including for example, control of transcription of T3 responsive genes in an in vitro cell assay system.

Incorporation of DNA sequences into procaryotic and eucaryotic host cells by standard transformation and transfection processes, potentially involving suitable viral and circular DNA plasmid vectors, is also within the contemplation of the invention and is expected to provide useful proteins in quantities heretofore unavailable from natural sources. Use of mammalian host cells is expected to provide for such post-translational modifications (e.g., truncation, glycosylation, and tyrosine, serine or threonine phosphorylation) as may be needed to confer optimal biological activity on recombinant expression products of the invention.

Novel protein products of the invention include polypeptides having the primary structural conformation (i.e., amino acid sequence) of hTRα1 protein, as set forth in FIG. 1A, FIG. 1B, and FIG. 1C, (therefor), as well as peptide fragments thereof and synthetic peptides assembled to be duplicative of amino acid sequences thereof. Proteins, protein fragments, and synthetic peptides of the invention are projected to have numerous uses including therapeutic uses and will provide the basis for preparation of monoclonal and polyclonal antibodies specifically immunoreactive with hTRα1. Preferred protein fragments and synthetic peptides include those duplicating regions of hTRα1 which are unique to hTRα1. The proteins of the invention are also expected to find utility in developing more effective tests of thyroid function.

Also provided by the present invention are polyclonal and monoclonal antibodies characterized by their ability to bind with high immunospecificity to hTRα1 proteins and to their fragments and peptides, recognizing unique epitopes which are not common to other proteins especially other human thryoid receptor proteins. The antibodies of the invention can be used for affinity purification of hTRα1 from other sources and cell types.

The present invention also provides novel procedures for the detection and/or quantification of normal, abnormal, or mutated forms, of hTRα1, as well as nucleic acids (e.g., DNA and mRNA) associated therewith. Illustratively, antibodies of the invention may be employed in known immunological procedures for quantitative detection of hTRα1 proteins in samples, and detection of DNA sequences of the invention (particularly those having sequences encoding hTRα1) that may be suitably labelled and employed for quantitative detection of mRNA encoding these proteins.

Among the multiple aspects of the present invention, therefore, is the provision of (a) novel hTRα1 encoding DNA sequence as set out in FIG. 1A, FIG. 1B, and FIG. 1C, (therefor), as well as (b) DNA sequences which hybridize thereto under hybridization conditions of the stringency equal to or greater than the conditions described herein and employed in the initial isolation of cDNAs of the invention, and (c) DNA sequences encoding the same allelic variant, or analog hTRα1 protein or polypeptide fragments, through use of, at least in part, degenerate codons. Correspondingly provided are vital or circular plasmid DNA vectors incorporating such DNA sequences in procaryotic and eucaryotic host cells transformed or transfected with such DNA sequences and vectors, as well as novel methods for the recombinant production of hTRα1 through cultured growth of such hosts and isolation of these proteins from the hosts or their culture media.

Other aspects and advantages of the present invention will be apparent upon consideration of the following detailed description thereof which includes numerous illustrative examples of the practice of the invention, reference being made to the drawing.

BRIEF DESCRIPTION OF FIGURES

FIG. 1A, FIG. 1B, and FIG. 1C, (therefor) is the nucleotide and deduced amino acid sequence of λMe2.

DETAILED DESCRIPTION

The following examples illustrate practice of the invention. Example 1 relates to complementary DNA cloning and sequencing. Example 2 relates to northern hybridization analysis. Example 3 relates to in vitro expression and hormone binding assay. Example 4 relates to use of hTRα1 DNA as a probe.

The examples which follow are for illustrative purposes only and are not intended in any way to limit the scope of the invention.

EXAMPLE 1

Complementary DNA Cloning and Sequencing:

Recombinant phage ($\sim 10^8$) from a human fetal muscle cDNA λgt10 library were screened using a nick-translated 1410 bp EcoR1 fragment from pke 711. Nakai, A., et al., *Proc. Nat'l. Acad. Sci. USA*, 85:2781–2785 (1988). The hybridization mixture contained 25% formamide, 1× Denhardt's, 5× SSC, 0.1% SDS, 100 μg/ml denatured salmon sperm DNA, and $0.5 \times 10^6$ cpm/ml [$^{32}$p] labelled EcoR1 fragment (SA $1 \times 10^8$ cpm/μg). Nitrocellulose filters were hybridized at 37° C. for 18 h. washed in 2× SSC, 0.1% SDS at room temperature for 1 h, and then washed at 42° C. for 30 min. The EcoR1 insert of λMe2 was sequenced using the Sanger dideoxy chain termination procedure (Sanger, F., et al., *Proc. Nat'l. Acad. Sci. (USA)*, 74:5463–5467 (1977)) and Sequenase (U.S. Biochemical Corp., Cleveland, Ohio). The nucleotide sequence of the coding region was determined on both strands.

Two clones in a fetal skeletal muscle cDNA library (Koenig, M., *Cell*, 50:509–511 (1987)) hybridized with the 1400 bp EcoR1 fragment of the hTRα1 clone, λke12. The partial sequence of one, λMe1, indicated that it encoded hTRα2. The sequence of λMe2 was 1888 bp with an open reading frame of 1230 bp, encoding a different form of the human thyroid hormone receptor, having 410 amino acids, and having a predicted molecular mass of 47 kD. The protein is designated hTRα1. The nucleotide sequence and deduced amino acid sequence is given in FIG. 1A, FIG. 1B, and FIG. 1C, (therefor.) Initiation and termination codons of a short reading frame in the 5'-untranslated region are underlined. The site of divergence of hTRα1 from hTRα2 is indicated by a triangle. Numbers above the translated sequence indicate amino acid residues. Nucleotides are numbered at the left of the sequence. The sequence from nucleotide 16 to 1183 of λMe2 is identical to that of the hTRα2 cDNA sequence (the sequence of hTRα2 corresponding to nucleotides 1–16 has not been determined). Correspondingly, the amino acid sequences of residues 1–370 of these two related human thyroid hormone receptors are identical; the COOH-terminal 40 residues of the hTRα1 sequence and 120 residues of hTRα2 are unique, as is the nucleotide sequence encoding this segment of each protein (the sequences of the 3'-untranslated regions of each type of clone are also unique). Although the COOH-terminal sequence of hTRα1 has no homology with that of hTRα2, it has 100% identity with the sequence of the cognate rat TR receptor sequence, rTRα1, over a span of 120 nucleotides. Moreover, the nucleotide sequences of the human and rat clones are also identical in the COOH-terminal coding region.

EXAMPLE 2

Northern Hybridization Analysis:

Human tissues were obtained at surgery, with permission of the Committee on Human Investigation, and RNA was isolated using the guanidinium thiocyanate procedure (Chirgwin, J. M., et al., *Biochemistry*, 18:5294–5299 (1979)). Poly(A) RNA was prepared by oligo(dT) chromatography. Poly(A) RNAs were separated on a 1% agarose gel containing formaldehyde, transferred to nitrocellulose, and probed using an oligolabeled 590 bp XhoI-EcoR1 fragment λMe2. Filters were hybridized overnight and washed with 0.2× SSC and 0.1% SDS at 60° C.

Hybridization of a 590 bp XhoI-EcoR1 fragment from the 3'end of λMe2, which is specific for hTRα1, to a Northern blot containing RNA prepared from adult human kidney and spleen, adolescent tonsils, and term placenta revealed specific hybridization to a 3.2 kb transcript in each tissue, and hybridization to a larger, less abundant transcript of about 6 kb. The insert in λMe2 is 1888 bp. Although the clone terminates with a region of 17 As, it is not clear that this tract corresponds to the poly(A) tail of the mRNA since the sequence preceding it not typical for a pre-polyadenylation sequence. An hTRα2 mRNA specific probe also hybridized to 3.2 kb transcripts in each of these tissues.

EXAMPLE 3

In Vitro Expression and Hormone Binding Assay:

The EcoR1 insert of λMe2 was inserted in the EcoR1 site of pGEM4Z (Promega Biotec, Madison, Wis.) to yield pMe21. pMe21 was linearized with Hind III and used as a template. for SP6 polymerase catalyzed synthesis of RNA (Melton, D. A., et al., *Nucleic Acids Res.*, 12:7035–7056 (1984)). Capped RNA was translated in a rabbit reticulocyte lysate (Promega Biotec). Thyroid hormone binding activity of the translated protein was assayed according to the method of Nakai, A., et al., *Proc. Nat'l. Acad. Sci. USA*, 85:2781–2785 (1988).

Translation of in vitro expressed hTRα1 mRNA resulted in the synthesis of two major proteins having sizes of 55 and 50 kilodaltons (kDa) as determined by sodium dodecyl sulfate (SDS)-polyacrylamide gel electrophoresis. It is unknown why the protein displays a higher molecular weight than the predicted molecular mass of 47 kD on SDS-polyacrylamide gel electrophoresis. A similar discrepancy was observed during in vitro synthesis of rTRα1 (Thompson, C. C., et al., *Science*, 237:1610–1614 (1987). Moreover, the synthesis of two major proteins was unexpected. Possibly, the larger 55 kDa protein corresponds to the expected 410 amino acid protein and the 50 kDa protein may correspond to hTRα1 39–410 since initiation of translation at Met 39 would result in the synthesis of a protein having a mass of about 4 kDa less.

The translated hTRα1 protein(s) were assayed for their biological activity by their ability to bind thyroid hormone. For example, it was found that the proteins bound T$_3$ (triiodothyronine) with an association constant (K$_a$) of $1.8 \times 10^9$ liter/M; this is similar to the affinity of translated hTRα2 for this ligand. In competition experiments, the translated hTRα1 protein possessed affinities for T$_4$ and triiodothyroacetic acid (Triac) similar to those of hTRα2, and characteristic of thyroid hormone receptors from human and animal tissues.

The sequence at the site of divergence of hTRα1 and hTRα2, AAG/GTGACT, includes the consensus sequence for the donor site of an exon-intron junction Lewin, B., *Cell*, 22:324–326 (1980). Although gene duplication and partial gene conversion have not been totally excluded, it is possible that alternative splicing is responsible for generating TRα proteins having COOH-termini of different lengths as well as sequence. Alternative splicing has previously been reported for human glucocorticoid receptor (Hollenberg, S. M., et al., *Nature*, 318:635–641 (1985)). However, in that instance, one of the two proteins did not bind glucocorticoids in vitro, and its mRNA was not detected by Northern blot analysis of RNA from several tissues. In contrast, both hTRα1 and hTRα2 bind T$_3$ and are present in many human tissues.

EXAMPLE 4

Use of hTRα1 DNA as a Probe:

use of hTRα1 DNA as probes to study the expression of receptor protein in human tissue samples, e.g., the distribution of mRNA in all types of human tissue is contemplated by, i.e., in situ hybridization or Northern blot hybridization analysis.

For the analysis of mRNA for hTRα1, or for related proteins, dot hybridization and Northern hybridization analyses can be used to characterize mRNA and hTRα1 or hTRα1-like molecules quantitatively and qualitatively. From these studies valuable information about the number of different forms of hTRα1 genes and their expression in different human tissues can be obtained.

It is also possible to use appropriate oligonucleotide fragments of hTRα1 DNA as primers to amplify genomic DNA, isolated from, for example, human leucocytes, by specific DNA polymerases. The amplified genomic DNA can then be analyzed to identify sequence abnormality using the polymerase chain reaction (PCR) assay. Saiki, et al., *Science*, 230:1350 (1985). See also, Mullis, K. B., U.S. Pat. No. 4,683,202; Jul. 28, 1987; and Mullis, K. B., U.S. Pat. No. 4,683,195; Jul. 28, 1987.

The foregoing illustrative examples relate generally to DNA sequences encoding thyroid hormone receptor and more particularly to hTRα1 thyroid receptor, to DNA sequences encoding hTRα1, to the polypeptide products of recombinant expression of these DNA sequences, to peptides whose sequences are based upon the amino acid sequences deduced from these DNA sequences, to antibodies specific for such proteins and peptides, and to procedures for the detection and quantitation of such proteins and nucleic acids related thereto, as well as to procedures relating to the development of therapeutic agents. While the present invention has been described in terms of specific methods and compositions, it is understood that variations and modifications will occur to those skilled in the art upon consideration of the present invention.

Numerous modifications and variations in the invention as described in the above illustrative examples are expected to occur to those skilled in the art and consequently only such limitations as appear in the appended claims should be placed thereon.

Accordingly it is intended in the appended claims to cover all such equivalent variations which come within the scope of the invention as claimed.

What is claimed is:

1. A purified and isolated nucleic acid molecule having a contiguous, uninterrupted sequence encoding human hTRα1 as defined by the amino acid sequence of FIG. 1A, FIG. 1B, and FIG. 1C.

2. The nucleic acid molecule of claim 1, further defined as a DNA molecule.

3. The nucleic acid molecule of claim 2, further defined as a cDNA molecule.

4. The nucleic acid molecule of claim 3, further defined as comprising the human hTRα1-encoding nucleotide sequence as set forth in FIG. 1A, FIG. 1B, and FIG. 1C, (therefor.)

5. A recombinant vector having a contiguous, uninterrupted sequence encoding human hTRα1 as defined by the amino acid sequence of FIG. 1A, FIG. 1B, and FIG. 1C, (therefor.)

* * * * *

UNITED STATES PATENT AND TRADEMARK OFFICE
CERTIFICATE OF CORRECTION

PATENT NO. : 5,438,126
DATED : August 1, 1995
INVENTOR(S) : Leslie J. DeGroot and Akira Nakai It is certified that error appears in the above-identified patent and that said Letters Patent is hereby corrected as shown below:

In claim 4, column 6, line 59, delete ",(therefor.)" and insert --.-- therefor.

In claim 5, column 5, line 63, delete ",(therefor.)" and insert --.-- therefor.

Signed and Sealed this

Tenth Day of October, 1995

Attest:

BRUCE LEHMAN

Attesting Officer

Commissioner of Patents and Trademarks